(12) United States Patent
Watson et al.

(10) Patent No.: US 9,339,809 B2
(45) Date of Patent: May 17, 2016

(54) DEOXYGENATION PROCESS

(75) Inventors: Michael John Watson, Eaglescliffe (GB); David Davis, Darlington (GB); Emily Fairnington Douglas, Dalkeith (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 13/387,586

(22) PCT Filed: Jul. 29, 2010

(86) PCT No.: PCT/GB2010/051254
§ 371 (c)(1),
(2), (4) Date: Jun. 7, 2012

(87) PCT Pub. No.: WO2011/012900
PCT Pub. Date: Feb. 3, 2011

(65) Prior Publication Data
US 2012/0238792 A1 Sep. 20, 2012

(30) Foreign Application Priority Data
Jul. 29, 2009 (GB) .................................. 0913193.9

(51) Int. Cl.
*B01J 37/08* (2006.01)
*B01J 23/42* (2006.01)
*B01J 29/44* (2006.01)
*B01J 29/12* (2006.01)
*B01J 29/74* (2006.01)
*B01J 35/00* (2006.01)
*B01J 37/02* (2006.01)
*C07C 1/24* (2006.01)
*C07C 5/05* (2006.01)
*C07C 13/18* (2006.01)
*C10G 3/00* (2006.01)
*B01J 23/40* (2006.01)
*B01J 23/70* (2006.01)
*B01J 23/755* (2006.01)

(52) U.S. Cl.
CPC *B01J 37/08* (2013.01); *B01J 23/42* (2013.01); *B01J 29/126* (2013.01); *B01J 29/44* (2013.01); *B01J 29/7415* (2013.01); *B01J 35/0006* (2013.01); *B01J 37/0201* (2013.01); *C07C 1/24* (2013.01); *C07C 5/05* (2013.01); *C07C 13/18* (2013.01); *C10G 3/45* (2013.01); *C10G 3/47* (2013.01); *C10G 3/48* (2013.01); *C10G 3/49* (2013.01); *C10G 3/50* (2013.01); *B01J 23/40* (2013.01); *B01J 23/70* (2013.01); *B01J 23/755* (2013.01); *B01J 2229/16* (2013.01); *C07C 2101/14* (2013.01); *C07C 2523/42* (2013.01); *C07C 2523/46* (2013.01); *C10G 2300/1096* (2013.01); *Y02P 20/52* (2015.11); *Y02P 30/20* (2015.11)

(58) Field of Classification Search
None
See application file for complete search history.

(56) References Cited

U.S. PATENT DOCUMENTS

| | | |
|---|---|---|
| 3,308,069 A | 3/1967 | Wadlinger et al. |
| 3,409,681 A | 11/1968 | Kroll |
| 3,912,787 A | 10/1975 | Nowack et al. |
| 4,665,274 A | 5/1987 | Ichihashi et al. |
| 4,992,605 A | 2/1991 | Craig et al. |
| 5,082,986 A | 1/1992 | Miller |
| 5,157,179 A | 10/1992 | Setoyama et al. |
| 5,248,841 A | 9/1993 | Young |
| 5,414,171 A | 5/1995 | Richard et al. |
| 5,424,264 A | 6/1995 | Richard et al. |
| 5,569,803 A | 10/1996 | Takewaki et al. |
| 5,705,722 A | 1/1998 | Monnier et al. |
| 2006/0161032 A1 | 7/2006 | Murzin et al. |
| 2006/0175231 A1 | 8/2006 | Hansen et al. |
| 2006/0207166 A1 | 9/2006 | Herskowitz et al. |
| 2006/0264684 A1 | 11/2006 | Petri et al. |
| 2007/0006523 A1 | 1/2007 | Myllyoja et al. |
| 2007/0010682 A1 | 1/2007 | Myllyoja et al. |
| 2007/0068848 A1 | 3/2007 | Monnier et al. |
| 2007/0135669 A1 | 6/2007 | Koivusalmi et al. |
| 2007/0281875 A1 | 12/2007 | Scheibel et al. |
| 2009/0031617 A1 | 2/2009 | O'Rear |
| 2009/0075813 A1 | 3/2009 | Whisenhunt et al. |
| 2009/0299109 A1* | 12/2009 | Gruber ...................... C10L 1/04 585/14 |
| 2011/0277378 A1* | 11/2011 | Von Hebel ............... C08H 8/00 44/436 |

FOREIGN PATENT DOCUMENTS

EP  0 501 577 A1  9/1992
EP  0 574 994 A1  12/1993
(Continued)

OTHER PUBLICATIONS

Osman Ilke Senol "Hydrodeoxygenation of aliphatic and Aromatic Oxygenates on Sulphided Catalysts for Production of Second Generation Biofuels" Helsinki University of Technology Nov. 30, 2007.*
(Continued)

*Primary Examiner* — Tam M Nguyen
(74) *Attorney, Agent, or Firm* — RatnerPrestia

(57) ABSTRACT

The invention is a process for the production of a hydrocarbon product including contacting an oxygenated aromatic feedstock, in the presence of hydrogen, with a catalyst composition including:
  a) a metal hydrogenation catalyst and
  b) a solid acid catalyst which is active for the deoxygenation of oxygenated hydrocarbons.

The process is useful for the conversion of pyrolysis oils and other products derived from biomass and plastics recycling etc, into fuels and chemical feedstocks.

16 Claims, No Drawings

(56) References Cited

FOREIGN PATENT DOCUMENTS

| EP | 0 653 399 A1 | 5/1995 |
|---|---|---|
| EP | 1 396 531 A2 | 3/2004 |
| EP | 2 019 132 A1 | 1/2009 |
| JP | 7-285892 A | 10/1995 |
| JP | 9-2981 A | 1/1997 |
| WO | WO-2006/100584 A2 | 9/2006 |
| WO | WO 2007/068796 A2 | 6/2007 |
| WO | WO 2007/068800 A2 | 6/2007 |
| WO | WO-2007/132938 A1 | 11/2007 |
| WO | WO 2007/144473 A1 | 12/2007 |
| WO | WO-2008/101945 A1 | 8/2008 |
| WO | WO-2008/109877 A1 | 9/2008 |
| WO | WO-2009/001712 A1 | 12/2008 |
| WO | WO-2009/039347 A1 | 3/2009 |
| WO | WO-2009/126508 A2 | 10/2009 |

OTHER PUBLICATIONS

International Search Report dated Mar. 28, 2011, from PCT International Application No. PCT/GB2010/051254.
British Search Report dated Jan. 12, 2010, from British Patent Application No. 0913193.9.
George Huber et al., "Processing biomass in conventional oil refineries: Production of high quality diesel by hydrotreating vegetable oils in heavy vacuum oil mixtures," *Applied Catalysis A: General*, vol. 329, 2007, pp. 120-129.
M.S. Zanuttini et al., "Deoxygenation of m-cresol on $Pt/\gamma-Al_2O_3$ catalysts," Catalysis Today 213 (2013) 9-17, Journal homepage: www.elsevier.com/locate/cattod.
Ezekiel O. Odebunmi et al., "Catalytic Hyrodeoxygenation," Journal of Catalysis 80, 56-64 (1983).
Douglas C. Elliott, "Historical Developments in Hydroprocessing Bio-oils," Energy & Fuels 2007, 21, 1792-1815.
Jelle Wildschut et al., "Hydrotreatment of Fast Pyrolysis Oil Using Heterogeneous Noble-Metal Catalysts," Ind. Eng. Chem. Res. 2009, 48, 10324-10334.
Robert O. Dunn, The Biodiesel Handbook, 2$^{nd}$ ed., edited by G. Knothe & J. Van Gerpen, AOCS Pressm 516, pp. 405-437 (2010).
Sotelo-Boyas, R. et al. (2012). "Hydroconversion of Triglycerides into Green Liquid Fuels," in Hydrogenation, Intech, pp. 187-216.
Mathias Snare et al., "Heterogeneous Catalytic Deoxygenation of Stearic Acid for Production of Biodiesel," Ind. Eng. Chem. Res. 2006, 45, 5708-5715.
Tom Kalnes et al. "Green Diesel: A Second Generation Biofuel," Intl. J of Chem. Reactor Eng., vol. 5 (2007).

\* cited by examiner

DEOXYGENATION PROCESS

CROSS-REFERENCE TO RELATED APPLICATIONS

This application is the U.S. National Phase application of PCT International Application No. PCT/GB2010/051254, filed Jul. 29, 2010, which claims priority of British Patent Application No. 0913193.9, filed Jul. 29, 2009, the disclosures of both of which are incorporated herein by reference in their entities for all purposes.

FIELD OF THE INVENTION

The present invention relates to a deoxygenation process for the conversion of oxygenated organic materials, for example pyrolysis oil, and its constituent compounds to aromatic and aliphatic hydrocarbons. The process is particularly useful for the treatment of pyrolysis oils derived from biomass such as wood and other plant fibres to make compounds useful for use as fuels and chemical feedstocks.

SUMMARY OF THE INVENTION

According to the invention we provide a process for the production of a hydrocarbon product comprising contacting a feedstock comprising at least one oxygenated aromatic compound, in the presence of hydrogen with a catalyst composition comprising:
a) a first catalyst comprising a metal-containing hydrogenation catalyst and
b) a second catalyst comprising a solid acid catalyst, said first and second catalysts being deployed in the same catalyst bed or in separate catalyst beds.

The feedstock may comprise a variety of oxygenated aromatic compounds which are typically found in pyrolysis oils, product streams from other biomass conversion processes, plastics recycling and depolymerisation. Pyrolysis oil is formed from the pyrolysis of biomass and is a dense, tarry substance that contains a high proportion of oxygenated aromatic compounds. We include in the definition of oxygenated aromatic compounds, compounds such as phenols, alkyl phenols, alkoxy-substituted aromatic compounds (for example anisole and substituted anisoles) and aromatic carbonyl compounds. The feedstock may also contain aliphatic oxygenates such as alcohols and carbonyls. The feedstock may be refined and/or purified to remove contaminants prior to contact with the catalyst. Such purification may include the steps of filtering, distillation, treating with absorbents for removal of sulphur- or nitrogen-containing compounds or the removal of metal compounds or other contaminants which may deleteriously affect the performance of the catalyst. The feedstock may be diluted with a suitable inert diluent, e.g. a hydrocarbon or mixture of hydrocarbons, if required. In such a case the diluent may optionally comprise a portion of the hydrocarbon product of the process.

We have found, unexpectedly, that the deoxygenation of aromatic species is facilitated by a preliminary hydrogenation step because the deoxygenation of cycloaliphatic compounds can be carried out at relatively low temperatures and at high conversions and selectivity relative to the deoxygenation of the corresponding aromatic compounds. Therefore using the process of the invention, the aromatic components of the feedstock may be converted to hydrocarbons in a low temperature process with little by-product formation and with very little carbon formation. The hydrocarbons formed may be used as chemical feedstocks or as fuels, optionally after further processing. Typical hydrocarbons found in the product stream include aromatic hydrocarbons and aliphatic hydrocarbons, including cyclic and non-cyclic hydrocarbons, which may be saturated or unsaturated.

DETAILED DESCRIPTION OF THE INVENTION

Without wishing to be bound by theory, the deoxygenation may be accomplished by dehydration of the oxygenated compounds following hydrogenation of the aromatic ring. This is illustrated for example purposes, showing the deoxygenation of an alkyl cyclohexanol by dehydration (in Scheme I). Hydrogenolysis of the (intermediate) aliphatic oxygenated compounds or of the oxygenated aromatic feedstocks may also occur but is not thought to be significant in the present process when operated under preferred process conditions. The mechanism is likely to depend on the process conditions such as temperature, pressure, feedstock composition, amount of hydrogen present and also on the nature of the solid acid catalyst.

(Scheme I)

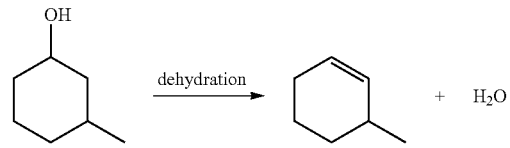

The process may be carried out in a single-step, i.e. by deploying the first and second catalysts in the same catalyst bed. Alternatively it may be operated in two or more steps, including at least one hydrogenation step wherein the feed is contacted with the first catalyst and at least one deoxygenation step in which a product stream from the hydrogenation step is contacted with the second (solid acid) catalyst. When the process is operated in more than one step, the contact of the feed with the metal hydrogenation catalyst must occur either before or simultaneously with the contact of the feed with the solid acid catalyst in order to ensure that the solid acid catalyst is brought into contact with some hydrogenated (de-aromatised) compounds. We have found that the operation of the process in two steps may be beneficial, particularly when the feedstock includes oxygenated aromatic compounds which require a reaction temperature greater than 150° C., in particular greater than 200° C. in order to hydrogenate the aromatic ring at an acceptable rate. By operating the hydrogenation catalyst in a separate catalyst bed from the solid acid catalyst, the reaction conditions selected for the hydrogenation reaction may be different from the reaction conditions for the deoxygenation reaction. We have found that if the deoxygenation reaction is operated at temperatures greater than about 200° C., the amount of heavy by-product produced as a result of side reactions may be unacceptably high. Without wishing to be bound by theory, we believe that these heavy by-products are associated with the coupling of cyclic olefins produced as a result of the dehydration of the saturated oxygenates and that this coupling is increased at higher temperatures. In the presence of hydrogen, the cyclic olefins are readily hydrogenated to form saturated cyclic hydrocarbon products. It is therefore preferred to operate the deoxygenation step in the presence of hydrogen in order to avoid the build-up of unsaturated compounds and thereby reduce the amount of heavy by-products formed by coupling reactions. Preferably at least some hydrogenation catalyst is also present in the deoxygenation step. In this way, the hydrogenation of olefinically unsaturated deoxygenated products may be promoted to reduce the amount of unwanted coupled products.

The metal-containing hydrogenation catalyst comprises at least one metal which is catalytically active for the hydrogenation of aromatic unsaturation. Catalysts which are useful for the hydrogenation of aromatic compounds, and their methods of manufacture, are well known to the skilled person. The metal is preferably selected from platinum, palladium, nickel, cobalt, copper, ruthenium, rhodium, rhenium and mixtures of two or more of these metals and is more preferably selected from platinum, palladium and nickel. Optionally the hydrogenation catalyst is promoted with other metals. The hydrogenation catalyst may be unsupported but is preferably supported on a suitable support which may be selected from any conventional support such as a silica alumina cogel, silica, a transition alumina such as gamma, delta or theta aluminas, carbon, titania, zirconia and sulphated zirconia. Mixtures of these support materials may also be used. The metal hydrogenation catalyst may be supported on at least a portion of the solid acid catalyst. More than one metal hydrogenation catalyst may be present in the catalyst composition.

The amount of metal hydrogenation catalyst present in the catalyst composition depends upon the nature of the metal(s) present and form of the catalyst. When the metal hydrogenation catalyst comprises at least one of Pt or Pd on a support, then the catalyst composition preferably contains from 0.01 to 10%, more preferably 0.1 to 5% by weight of the metal hydrogenation catalyst. When the catalyst is a supported nickel, cobalt or copper then the catalyst typically contains up to about 40% by weight of metal, e.g. 10-25 wt %. Other forms of catalyst such as a sponge metal or Raney™ nickel may contain very little, if any support. The physical form of the catalyst also affects the amount of metal used; when the catalyst is in the form of a powder then the concentration of metal is higher than when the catalyst is in the form of larger pellets. When the catalyst is in the form of larger particles or pellets (for example having a minimum dimension greater than 1 mm), the metal may be concentrated in the portion of the catalyst pellet near the surface of the pellet—i.e. as an "eggshell" catalyst. The metal is preferably deposited on the surface of a porous support and/or within the pores in such a support.

Supported metal catalysts may be formed by impregnating the support with a solution of a compound of the metal, followed by drying and, optionally, calcining the dried material. Alternative methods include precipitation of a compound of the metal hydrogenation catalyst onto the support or with the support, including precipitation-deposition methods in which a metal complex, e.g. a metal amine complex, is decomposed by heating in the presence of the support. Alternatively, the metal hydrogenation catalyst may be introduced onto the support by ion-exchange if the selected support is susceptible to such methods. The metal is preferably present in the form of elemental metal and so the metal hydrogenation catalyst compound on the support is reduced to the form of elemental metal. The reduction step may be carried out prior to placing the catalyst in the reactor, e.g. by effecting reduction of the solid catalyst particles by contact with a hydrogen-containing gas or by "wet" reduction with a reducing agent such as a hydrazine. Alternatively the metal hydrogenation catalyst compound on the catalyst support may be reduced to metal hydrogenation catalyst in elemental form in the reactor by contacting the catalyst with a hydrogen-containing gas stream for a suitable time to effect reduction. Methods of forming a catalyst by the techniques discussed above and others are known in the art and will be familiar to the skilled person. Catalysts comprising the metal hydrogenation catalyst on a support are known in the art and are available commercially.

The solid acid catalyst is active for the deoxygenation of oxygenated organic compounds to form deoxygenated compounds, especially to form hydrocarbons from oxygenated aromatic and cycloaliphatic compounds such as substituted phenols and cyclohexanols. A suitable solid acid is preferably a solid material that demonstrates sufficient acidity to protonate pyridine. The use of pyridine as a probe molecule coupled with Fourier transform Infra-Red (FTIR) spectroscopy is known as a method to investigate the acidity of solids. Pyridine is protonated by reaction with Brønsted acid sites of sufficient strength. When pyridine interacts with such acid sites on a surface, an absorption at about 1546 $cm^{-1}$ can be observed by FTIR, allowing quantification of Brønsted acid sites. The pKa of the conjugate acid of pyridine is 5.2, therefore any acid with a pKa below this value will result in some degree of protonation of pyridine. Suitable solid acids therefore have a pKa<5.2. The solid acid catalyst is active for the deoxygenation (by dehydration and/or demethoxylation) of cyclohexanol and methoxycyclohexane at the selected reaction conditions. The solid acid catalyst is therefore preferably a material which is sufficiently acidic to protonate cyclohexanol and methoxycyclohexane.

The solid acid catalyst is preferably selected from zeolites, clays, acid treated metal oxides (for example sulphated zirconia, borated zirconia), acid treated mixed metal oxides, supported heteropoly acids, metal oxides and mixed metal oxides (e.g. tungsten or molybdenum oxides in combination with titania and zirconia, alumina-silicates, alumina, silica), silico-alumino-phosphates, sulphated carbon, proton exchange membranes such as Nafion™, acidic ion exchange resins and immobilised Lewis acid catalysts. Preferred zeolites include ferrierite, mordenite, ZSM-5, beta and faujasite, including zeolite Y. Zeolites having a molar ratio of silica to alumina of between 20 and 90, especially 20-50 have been found to be effective in the reaction but other zeolite compositions may also be useful. Silico-alumino-phosphates useful in the invention include, for example, SAPO-11 and SAPO-31. The provision of additional solid acid catalyst or the presence of metal hydrogenation catalyst on a different support may provide a means to provide sufficient metal hydrogenation catalyst and also sufficient acidic sites in the solid acid catalyst.

All of the metal hydrogenation catalyst present in the catalyst composition may be supported on particles of the solid acid catalyst. Alternatively there may be present in the catalyst composition a metal hydrogenation catalyst supported on the solid acid catalyst in addition to metal hydrogenation catalyst supported on an alternative support. As a further alternative all of the metal hydrogenation catalyst may be present on a support which is not a solid acid catalyst.

Optionally a promoter metal is also present in the catalyst composition. A promoter metal, if present may be associated with and present on the metal hydrogenation catalyst or a support and/or present on or in the solid acid catalyst.

The metal hydrogenation catalyst and the solid acid catalyst may be present in the reaction space in the form of powders or as formed particles suitable for forming fixed catalyst beds. The form of such particles to provide adequate strength in a catalyst bed and adequate mass and heat transfer characteristics under the desired reaction conditions may be selected by the skilled person. Typically such formed particles have a minimum dimension of at least 1 mm and often a maximum dimension less than 50 mm. Usually such particles are formed from powders by known methods such as tabletting, extrusion or granulation. Frequently additives such as a binder, lubricant or another additive may be present as is conventional in particle forming. The formed particles may have any of a variety of shapes as is known in catalyst manufacture. Typical shapes include tablets, cylinders, fluted cylinders, spheres, rings, wheel-shapes, lobed cylinders, optionally with one or more apertures in the cross-sectional shape.

In a first embodiment of the invention, the metal hydrogenation catalyst is dispersed on a support formed from the solid acid catalyst. In this embodiment, the metal hydrogenation catalyst may comprise, for example, Pt on faujasite (such as zeolite Y), Pt on SAPO-11, Pt on ZSM-5 or Pt on beta zeolite. Optionally an additional quantity of the solid acid catalyst may be present, either mixed with the supported metal hydrogenation catalyst or separated from it such that the feed stream contacts the additional solid acid catalyst downstream of the supported metal hydrogenation catalyst. When more than one metal hydrogenation catalyst is used, each metal may be disposed on the same solid acid catalyst or a different one. When the same solid acid catalyst is used, each metal may be present on the same particles of solid acid catalyst or they may be present on different particles, which may then be mixed together or disposed in separate parts of the reaction space.

In another embodiment of the invention, the metal hydrogenation catalyst(s), preferably on a support, is physically mixed with separate particles of the solid acid catalyst. As an example of this embodiment, the catalyst composition comprises a mixture of a particulate zeolite with a particulate supported palladium catalyst. When more than one metal hydrogenation catalyst is used, each metal may be disposed on the same support or a different one. It is also contemplated that more than one metal hydrogenation catalyst may be deposited on the same support particles using co-deposition/co-impregnation or by depositing the second metal hydrogenation catalyst upon a pre-existing metal hydrogenation catalyst+support combination. By physical mixture, we intend that particles of the supported metal and particles of the solid acid catalyst are mixed together. If required, such a mixture may subsequently be formed into a larger particle by a method such as tabletting, extrusion or granulation. In such a case a binder, lubricant or another additive may be present as is conventional in particle forming.

As a further embodiment, a first supported metal hydrogenation catalyst may be mixed with separate particles comprising a second metal hydrogenation catalyst (which may be the same as or different from the first metal hydrogenation catalyst) supported on a solid acid catalyst. As an example of this embodiment, the catalyst composition comprises a mixture of a palladium or platinum supported on a particulate zeolite with a particulate palladium-on-carbon catalyst. Optionally an additional quantity of solid acid catalyst may be present in the mixture or disposed as a separate bed downstream of the mixture.

A quantity of another solid particulate material may be present in the catalyst composition or in a bed containing the catalyst composition to aid dispersion, heat transfer or moderate activity in a catalyst bed. Such particles may include metal oxide materials such as alumina, silica etc.

A hydrogen-containing gas is present in the reaction mixture. The hydrogen-containing gas may comprise pure hydrogen or a mixture of hydrogen with a diluent which is inert under the selected reaction conditions. Suitable inert gases include nitrogen, helium or argon. Suitable hydrogen pressures that may be used are in the range from about 0.1 to about 100 bar at reaction temperature. The amount of hydrogen present in the reaction may influence the mechanism of deoxygenation.

It is preferred that the reaction takes place by contact of the oxygenated feedstock in the liquid phase with the hydrogen-containing gas in contact with a solid catalyst composition. The catalyst is preferably provided in the form of solid particles having a minimum dimension of at least 1 mm arranged as a fixed bed in a reactor designed to allow contact and flow of the liquid-phase fatty feedstock and a gas phase, if present, over the catalyst particles through the fixed bed, usually in the form of a "trickle bed" arrangement. Alternatively the catalyst may be provided in a structured form, such as a monolith coated with the catalyst composition and arranged such that the liquid and gas-phase reactants contact each other as they flow through channels in the monolith. As a further alternative, the reaction may take place in a slurry phase, the catalyst being provided in the form of small particles or a powder which is dispersed as a slurry within the liquid phase reactant whilst the hydrogen-containing gas is bubbled through the slurry or dispersed within the liquid in a saturator. The reaction may take place in the presence of a solvent, and may take place in conditions designed to maintain the solvent in a supercritical or near-supercritical state.

For the single stage reaction, in which the feed is contacted with the hydrogenation catalyst and the solid acid catalyst at the same time, the reaction temperature is preferably in the range from about 50° C. to about 400° C., more preferably 80-250° C., especially about 120-200° C. At higher temperatures, particularly at or above about 350° C., the feed and products may be cracked or coupled to produce compounds having with different numbers of carbon atoms than the starting material, Carbon may also be formed and deposited on the catalyst at higher temperatures, causing deactivation. The ability to operate the deoxygenation process effectively at low temperatures (e.g. <200° C.) is a particular benefit because cracking/coupling reactions can be avoided or reduced. Preferably, in order to maintain the liquid phase and drive the reaction, the pressure in the reactor is elevated to a suitable level.

Whether the reaction is carried out in one step or more than one step, it is preferred to maintain the reaction temperature in contact with the second (solid acid) catalyst at a temperature not greater than 250° C., more preferably not greater than 225° C., more preferably not greater than 200° C.

The reaction may be carried out in two or more steps, including a first step of contacting the oxygenated aromatic feedstock, in the presence of hydrogen, with a metal hydrogenation catalyst and then, in a second step, contacting the product of said first step with a solid acid catalyst which is active for the deoxygenation of hydrocarbons. When operating a multi-step process, the first and second steps may be carried out in different reactors using the same or different process conditions in each reactor. When the reaction is carried out in at least two steps such that the first and second catalysts are in different catalyst beds, the temperature of the bed containing the first (hydrogenation) catalyst may be different from the temperature of a bed containing the solid acid catalyst. It is preferred to maintain the temperature in the bed of the solid acid catalyst below 225° C., more preferably at or below 200° C. and more preferably below about 175° C. in order to minimise the formation of coupled products. The use of a two-step reaction enables the hydrogenation temperature to be optimised independently of the temperature of the deoxygenation reaction so that compounds which are more difficult to hydrogenate, such as substituted anisoles for example, may be hydrogenated at a temperature above 200° C. and then the hydrogenated product may be deoxygenated over the solid acid catalyst at a lower temperature, which is preferably 200° C. or less, selected to avoid coupling reactions. In the two-step process, the presence in the deoxygenation step of hydrogen and preferably also at least some hydrogenation catalyst is preferred in order that unsaturated olefins which may form as intermediate products are hydrogenated to saturated products. The unsaturated olefin intermediates are otherwise susceptible to react to form coupled products which are less desirable than the uncoupled saturated hydrocarbon products.

The process of the invention will be further described in the following examples.

EXAMPLES

Preparation Method A: Catalyst Preparation

Solid acid zeolites were supplied by Zeolyst International. Catalyst samples containing Pt on a solid acid support were prepared by incipient wetness impregnation of the supporting solid acid (in the hydrogen form) with an aqueous platinum nitrate solution. Each of the samples was then subjected to the following temperature programme under flowing air (10 L/min):
Ramp room temperature to 70° C. at 1° C./min and hold at 70° C. for 4 hrs.
Ramp 70° C. to 110° C. at 1° C./min and hold at 110° C. for 4 hrs.
Ramp 110° C. to 500° C. at 1° C./min and hold at 500° C. for 4 hrs.
Cool to room temperature.

After the calcination procedure the catalysts was sieved to 38-150 micons before use.

Pd and Rh on zeolite catalysts were made using the same method, but using Pd nitrate or Rh nitrate. Pd on zeolite catalyst was made using a final calcination temperature of 450° C. instead of 500° C. Pt on $Al_2O_3$ was made using the same method as given for Pt on zeolite but using a calcined transition alumina support powder instead of the zeolite.

Process Method General Reaction Procedure: Conversion of m-Cresol to Methylcyclohexane 1.54 g of m-cresol, 17.63 g of dodecane solvent and 0.10 g of catalyst (shown in Table 1) were charged into an autoclave. M-cresol was used to represent a model oxygenated aromatic compound. The vessel was purged twice with hydrogen, and the pressure was then set to the value shown. The autoclave was heated, with stirring at 800 rpm, to the desired reaction temperature over a period of 1 hour. This temperature was maintained for a period of 2 hours. Following the reaction, the autoclave was allowed to cool and vented. Liquid products were analysed by gas chromatography. Conversions of m-cresol and selectivities to different products are presented in Table 1. The hydrocarbon products include methylcyclohexane, toluene and methyl cyclohexene isomers. Selectivities to oxygenated reaction intermediates, methyl cyclohexanol and methyl cyclohexanone are also provided in Table 1. Unidentified products shown in the Table are believed to represent heavier compounds formed, for example, by the coupling of either oxygenated intermediates or hydrocarbon products, particularly cyclic olefins.

Examples 1-8 and 11-17

These examples show the effect of varying the reaction temperature and the nature of the metal and solid acid. Platinum, palladium and rhodium supported on the solid acids used are all shown to be effective catalysts to convert m-cresol to methylcyclohexane product. Comparison of examples 1-4 shows that, of the reaction temperatures used, 150° C. enables complete conversion to methylcyclohexane whilst forming fewer unidentified (probably coupled) byproducts than the reaction at 200° C.

In the Tables, the solid acid catalyst used is indicated by:
Y30=Y zeolite having silica/alumina=30 (Zeolyst™ CBV 720)
Y80=Y zeolite having silica/alumina=80 (Zeolyst™ CBV 901)
B38=Beta zeolite having silica/alumina=38 (Zeolyst CP 814C)
Z23=ZSM-5 zeolite having silica/alumina=23 (Zeolyst CBV 2314)
Z50=ZSM-5 zeolite having silica/alumina=50 (Zeolyst CBV 5524G)
Z80=ZSM-5 zeolite having silica/alumina=80 (Zeolyst CBV 8014)

Abbreviations Used in the Table:
Me cy'ane=methyl cyclohexane; Me cy'ene=sum of methyl cyclohexene isomers; Me cy'ol=methyl cyclohexanol; Me cy'one=methyl cyclohexanone; UID=Unidentified Products.
C=Carbon support; $Al_2O_3$=alumina support
* denotes a comparative example.

Comparative Example 9 & 10

Comparative Example 9 shows the effect of using no metal hydrogenation catalyst in the m-cresol conversion reaction described above. The B38 solid acid catalyst is seen to be ineffective in converting the feedstock under the conditions used. Comparative Example 10 shows the effect of using a commercial palladium on carbon catalyst instead of the combined catalyst composition of the present invention. Although the catalyst is capable of converting the feedstock at 245° C., the product contains mostly oxygenated intermediates, indicating that the Pd/C catalyst is less effective for deoxygenation than the combined catalyst used in the process of the invention.

Example 18 (Comparative)

A catalyst comprising 1% platinum on a calcined transition alumina support powder was made using the incipient wetness method described in Catalyst Preparation A. This catalyst is designated in Table 2 as $Pt/Al_2O_3$. The catalyst was used in the conversion of m-cresol as described in Process Method B above. The results, shown in Table 2 indicate that the main product was methylcyclohexanol so although the m-cresol feed was hydrogenated to yield the corresponding cycloaliphatic product, little deoxygenation was seen to have occurred.

Example 19

100 mg of the $Pt/Al_2O_3$ catalyst described in Example 18 was mixed with 100 mg of solid acid B38 and the mixture (200 mg) was used as the catalyst in the conversion of m-cresol as described in Process Method B above. The results, shown in Table 2 show 100% conversion to the methylcyclohexane product when the combination of the metal hydrogenation catalyst and the solid acid catalyst is used.

Examples 20 (Comparative) & 21

A commercial nickel/alumina catalyst (HTC 400™ available from Johnson Matthey Catalysts) was used alone (Example 20) and also as a physical mixture with an equal weight of B38 (Example 21). These experiments show that a combination of a nickel hydrogenation catalyst and a solid acid catalyst is effective for the conversion of m-cresol to methylcyclohexane.

Examples 22-25 (all comparative)

A commercial 5 wt % Pd on carbon catalyst was used in the conversion of ortho-, meta- and para-cresols according to the general procedure in B above, Table 3 shows that although some deoxygenation to methylcyclohexane is seen using the Pd/C catalyst at 225° C., the main products are oxygenated cyclohexanes with little deoxygenation evident at the lower temperatures. In Example 25, the reaction was carried out using 50 mg of a catalyst consisting of 2 wt % Ru on alumina.

Examples 26-29 (all comparative)

2-, 3- and 4-methylcyclohexanols (respectively the methylcyclohexanol isomers resulting from the hydrogenation of o-, m- and p-cresols used in Examples 22-25) were used as the feed in the reaction carried out using the same procedure as in B. The results in Table 3 show that the B38 solid acid is active for the deoxygenation of these saturated feed compounds. However, when no hydrogenation metal is present (Example 26) the most prevalent product was methylcyclohexene.

Examples 30-33

Process method C. Two step conversion of aromatic oxygenates 1.54 g of a methylanisole, 17.63 g of dodecane solvent and 0.10 g of metal catalyst (shown in Table 4—either Pd/C or Ni/Al$_2$O$_3$) were charged into an autoclave. The vessel was purged twice with hydrogen, and the pressure was then set to the value shown. The autoclave was heated, with stirring at 800 rpm, to the desired reaction temperature over a period of 1 hour. This temperature was maintained for a period of 2 hours. Following the reaction, the autoclave was allowed to cool and vented. An additional solid acid catalyst (100 mg) was then added to the reaction vessel. The vessel was purged twice with hydrogen, and the pressure was then set to the value shown. The autoclave was heated, with stirring at 800 rpm, to the desired reaction temperature (the second value in the reaction temperature column) over a period of 1 hour. This temperature was maintained for a period of 2 hours. Following the reaction, the autoclave was allowed to cool and vented. Liquid products were analysed by gas chromatography.

The results of Examples 30-33 are shown in Table 4 and show that conversion and selectivity to deoxygenated products are both high.

Examples 34-37

Examples 34-37 were carried out in a single step using the method described in method B above. Example 34 was carried out using a mixture of the B38 zeolite with commercial nickel/alumina catalyst as described in Example 21. Examples 35-37 were carried out using a precious metal supported on the B38 solid acid, made as described in A above. These examples show that using the catalyst comprising metal on B38 or a metal catalyst mixed with B38, the amount of unidentified heavy by-product is considerably greater than that obtained using the two-stage method of Examples 30-32 in which the hydrogenation is carried out with Pd at 225° C. and then the deoxygenation over the solid acid catalyst is carried out at a lower temperature. These examples demonstrate that the presence of the solid acid deoxygenation catalyst during hydrogenation reaction is less desirable when the hydrogenation is carried out at relatively high temperature. Example 34 appears to produce significantly more methylcyclohexanone than Example 33 using the same materials. Methylcyclohexanone is an intermediate hydrogenation product and it is likely that it would have been converted to methylcyclohexanol and then deoxygenated if the reaction had been continued.

Examples 38-40

O-cresol was used in Examples 38 & 39 as the feed material (instead of methylanisole) for a two-stage conversion according to Process Method C described above. The metal catalyst was 5% Pd on C or commercial 16% Ni on alumina as shown in Table 5. The conversion and selectivity to methylcyclohexane is very high. Example 40 uses the same catalyst combination as Example 39 but as a mixed catalyst in a one-step process according to Process Method B. The results in Table 5 show that, compared with the two-step process of Example 39, Example 40 produces a significantly higher concentration of by-products and therefore the selectivity to methylcyclohexane is substantially lower. This is likely to be due to the relatively high reaction temperature of the reaction in the presence of the solid acid catalyst.

Examples 41-42

0.26 g of each of m-cresol, o-cresol, p-cresol, 2-methylanisole, 3-methylanisole and 4-methylanisole, in addition to 17.63 g of dodecane solvent were mixed and used as the feed for a two-step reaction as described in Process Method C. The results, in Table 6, show that the process is effective for a feedstock containing a mixture of oxygenated aromatic compounds. The methylcyclohexane product is obtained in high yield.

Example 43

Example 43 uses the same mixed feed as Examples 41 & 42 but the catalyst is 16% Ni on alumina and B38 mixed catalyst in a one-step process according to Process Method B. Although this one-step process is effective for making methylcyclohexane, a significantly larger amount of unidentified by-product is made than when using the two step process with a similar catalyst combination in Example 41.

TABLE 1

| Example Number | Metal (M) in catalyst | Amount M (wt %) | Solid acid | Reaction Temp. (° C.) | H$_2$ pressure (bar) | Conversion (%) | Product Selectivity (%) | | | | | |
|---|---|---|---|---|---|---|---|---|---|---|---|---|
| | | | | | | | Me cy'ane | Me cy'ene | toluene | Me cy'ol | Me cy'one | UID |
| 1 | Pt | 1 | B38 | 100 | 20 | 97 | 25 | 0 | 3 | 48 | 8 | 16 |
| 2 | Pt | 1 | B38 | 125 | 20 | 100 | 46 | 0 | 1 | 42 | 0 | 11 |

TABLE 1-continued

| Example Number | Metal (M) in catalyst | Amount M (wt %) | Solid acid | Reaction Temp. (° C.) | H$_2$ pressure (bar) | Conversion (%) | Product Selectivity (%) | | | | | |
|---|---|---|---|---|---|---|---|---|---|---|---|---|
| | | | | | | | Me cy'ane | Me cy'ene | toluene | Me cy'ol | Me cy'one | UID |
| 3 | Pt | 1 | B38 | 150 | 20 | 100 | 99 | 0 | 0 | 0 | 0 | 1 |
| 4 | Pt | 1 | B38 | 200 | 20 | 99 | 89 | 1 | 2 | 0 | 0 | 8 |
| 5 | Pt | 0.3 | B38 | 100 | 20 | 49 | 17 | 1 | 2 | 46 | 21 | 14 |
| 6 | Pt | 7 | B38 | 100 | 20 | 100 | 25 | 0 | 0 | 63 | 0 | 12 |
| 7 | Pt | 1 | Y30 | 100 | 20 | 94 | 17 | 0 | 2 | 58 | 8 | 16 |
| 8 | Pt | 0.3 | Y80 | 100 | 10 | 63 | 17 | 1 | 2 | 49 | 18 | 13 |
| 9* | — | | none | 200 | 20 | 0 | 0 | 0 | 0 | 0 | 0 | 0 |
| 10* | Pd/C | 5 | — | 245 | 20 | 100 | 30 | 0 | 0 | 62 | 0 | 8 |
| 11 | Pd | 1 | B38 | 150 | 20 | 100 | 71 | 0 | 0 | 0 | 0 | 29 |
| 12 | Rh | 1 | B38 | 150 | 20 | 100 | 89 | 0 | 0 | 0 | 0 | 10 |
| 13 | Pt | 0.3 | B38 | 150 | 10 | 100 | 92 | 0 | 0 | 0 | 0 | 7 |
| 14 | Pt | 0.3 | B38 | 150 | 60 | 100 | 90 | 0 | 1 | 0 | 1 | 8 |
| 15 | Pt | 1 | Z23 | 150 | 20 | 100 | 67 | 0 | 0 | 26 | 0 | 6 |
| 16 | Pt | 1 | Z50 | 150 | 20 | 100 | 94 | 0 | 0 | 0 | 0 | 6 |
| 17 | Pt | 1 | Z80 | 150 | 20 | 100 | 88 | 0 | 0 | 9 | 0 | 2 |

TABLE 2

| Example Number | Metal (M) in catalyst | Amount M (wt %) | Solid acid | Reaction Temp. (° C.) | H$_2$ pressure (bar) | Conversion (%) | Product Selectivity (%) | | | | | |
|---|---|---|---|---|---|---|---|---|---|---|---|---|
| | | | | | | | Me cy'ane | Me cy'ene | toluene | Me cy'ol | Me cy'one | UID |
| 18* | Pt/Al$_2$O$_3$ | 1 | — | 150 | 20 | 100 | 2 | 0 | 0 | 79 | 0 | 19 |
| 19 | Pt/Al$_2$O$_3$ | 1 | B38 (mix) | 150 | 20 | 100 | 100 | 0 | 0 | 0 | 0 | 0 |
| 20* | Ni/Al$_2$O$_3$ | 16 | — | 175 | 20 | 100 | 0 | 1 | 0 | 96 | 0 | 3 |
| 21 | Ni/Al$_2$O$_3$ | 16 | B38 (mix) | 175 | 20 | 100 | 85 | 1 | 0 | 0 | 0 | 13 |

TABLE 3

| Example Number | feed | Metal (M) in catalyst | Amount M (wt %) | Solid acid | Reaction Temp. (° C.) | H$_2$ pressure (bar) | Conversion (%) | Product Selectivity (%) | | | | | |
|---|---|---|---|---|---|---|---|---|---|---|---|---|---|
| | | | | | | | | Me cy'ane | Me cy'ene | toluene | Me cy'ol | Me cy'one | UID |
| 22* | o-cresol | Pd | 5 | C | 225 | 20 | 100 | 14 | 0 | 0 | 75 | 10 | 2 |
| 23* | m-cresol | Pd | 5 | C | 100 | 20 | 100 | 1 | 0 | 0 | 65 | 21 | 13 |
| 24* | p-cresol | Pd | 5 | C | 125 | 20 | 98 | 1 | 0 | 0 | 20 | 63 | 16 |
| 25* | m-cresol | Ru | 2 | Al$_2$O$_3$ | 150 | 20 | 100 | 1 | 0 | 0 | 93 | 0 | 6 |
| 26* | 3-Me cy'ol | — | | none | B38 | 150 | 20 | 100 | 8 | 57 | 1 | — | 0 | 34 |
| 27* | 2-Me cy'ol | Pt | 1 | B38 | 150 | 20 | 100 | 94 | 0 | 0 | — | 0 | 6 |
| 28* | 3-Me cy'ol | Pt | 1 | B38 | 150 | 20 | 100 | 100 | 0 | 0 | — | 0 | 0 |
| 29* | 4-Me cy'ol | Pt | 1 | B38 | 150 | 20 | 100 | 92 | 0 | 0 | — | 0 | 8 |

TABLE 4

| Ex | feed | Metal (M) in catalyst | Conc M (wt %) | Solid acid | Reaction Temp. (° C.) | H$_2$ pressure (bar) | Conversion (%) | Product Selectivity (%) | | | | | | |
|---|---|---|---|---|---|---|---|---|---|---|---|---|---|---|
| | | | | | | | | Me cy'ane | Me cy'ene | toluene | Sum of 1-methoxy-3-Mecy'ane isomers | Me cy'ol | Me cy'one | Sum of cresol isomers | UID |
| 30 | 3-methylanisole | Pd/C | 5 | then B38 | 100 then 175 | 20 | 100 | 89 | 0 | 0 | 0 | 0 | 0 | 1 | 10 |
| 31 | 2-methylanisole | Pd/C | 5 | then B38 | 125 then 175 | 20 | 99 | 88 | 0 | 0 | 0 | 0 | 0 | 1 | 11 |
| 32 | 4-methylanisole | Pd/C | 5 | then B38 | 100 then 175 | 20 | 100 | 89 | 0 | 0 | 0 | 0 | 0 | 1 | 10 |
| 33 | 2-methylanisole | Ni/Al$_2$O$_3$ | 16 | then B38 | 225 then 175 | 20 | 99 | 87 | 0 | 0 | 0 | 0 | 0 | 0 | 12 |

TABLE 4-continued

| Ex | feed | Metal (M) in catalyst | Conc M (wt %) | Solid acid | Reaction Temp. (° C.) | H$_2$ pressure (bar) | Conversion (%) | Product Selectivity (%) | | | | | | | |
|---|---|---|---|---|---|---|---|---|---|---|---|---|---|---|---|
| | | | | | | | | Me cy'ane | Me cy'ene | toluene | Sum of 1-methoxy-3-Mecy'ane isomers | Me cy'ol | Me cy'one | Sum of cresol isomers | UID |
| 34 | 2-methylanisole | Ni/Al$_2$O$_3$ | 16 | B38 (mix) | 225 | 20 | 100 | 69 | 0 | 0 | 0 | 0 | 19 | 0 | 12 |
| 35 | 3-methylanisole | Pt | 1 | B38 | 200 | 20 | 34 | 2 | 0 | 0 | 0 | 0 | 0 | 37 | 61 |
| 36 | 3-methylanisole | Pd | 1 | B38 | 200 | 20 | 82 | 51 | 1 | 1 | 1 | 0 | 4 | 1 | 41 |
| 37 | 3-methylanisole | Rh | 1 | B38 | 200 | 20 | 99 | 56 | 0 | 0 | 0 | 0 | 0 | 1 | 43 |

TABLE 5

| Example | Metal (M) in catalyst | conc M (wt %) | Solid acid | Reaction Temp. (° C.) | H$_2$ pressure (bar) | Conversion (%) | Product Selectivity (%) | | | | | |
|---|---|---|---|---|---|---|---|---|---|---|---|---|
| | | | | | | | Me cy'ane | Me cy'ene | toluene | Me cy'ol | Me cy'one | UID |
| 38 | Pd/C | 5 | then B38 | 225 then 150 | 20 | 100 | 97 | 0 | 0 | 0 | 0 | 3 |
| 39 | Ni/Al$_2$O$_3$ | 16 | then B38 | 225 then 150 | 20 | 100 | 100 | 0 | 0 | 0 | 0 | 0 |
| 40 | Ni/Al$_2$O$_3$ | 16 | B38 (mix) | 225 | 20 | 100 | 38 | 0 | 1 | 0 | 24 | 37 |

TABLE 6

| Example | Metal (M) in catalyst | Conc M (wt %) | Solid acid | Reaction Temp. ° C. | H$_2$ pressure (bar) | Total Conv. (%) | MA Conv (%) | Cresol Conv. (%) | Product Selectivity (%) | | | | | | |
|---|---|---|---|---|---|---|---|---|---|---|---|---|---|---|---|
| | | | | | | | | | Me cy'ane | Me cy'ene | Toluene | Sum of 1-methoxy-3-Mecy'ane isomers | Me cy'ol | Me cy'one | UID |
| 41 | Ni/Al$_2$O$_3$ | 16 | then B38 | 225 then 175 | 20 | 99 | 100 | 94 | 94 | 0 | 0 | 0 | 0 | 0 | 6 |
| 42 | Pd/C | 5 | then B38 | 225 then 175 | 20 | 99 | 100 | 99 | 96 | 0 | 0 | 0 | 0 | 0 | 3 |
| 43 | Ni/Al$_2$O$_3$ | 16 | B38 mix | 225 | 20 | 85 | 71 | 97 | 67 | 2 | 1 | 0 | 0 | 0 | 29 |

The invention claimed is:

1. A process for the production of a hydrocarbon product comprising deoxygenating at least one oxygenated aromatic compound by contacting a feedstock comprising the at least one oxygenated aromatic compound, in the presence of hydrogen, with:
   a) a metal hydrogenation catalyst and
   b) a solid acid catalyst which is active for the deoxygenation of oxygenated hydrocarbons, the solid acid catalyst having a pKa<5.2.

2. A process as claimed in claim 1, wherein said metal hydrogenation catalyst is selected from the group consisting of platinum, palladium, nickel, cobalt, copper, ruthenium, rhodium and rhenium and mixtures thereof.

3. A process as claimed in claim 1, wherein said metal hydrogenation catalyst is present in dispersed form supported on particles of a support material.

4. A process as claimed in claim 3, wherein said support material comprises particles of said solid acid catalyst.

5. A process as claimed in claim 3, wherein said support material comprises particles of a material selected from the group consisting of silica-alumina, silica, a transition alumina, carbon, titania, zirconia and mixtures of two or more of these materials.

6. A process as claimed in claim 1, wherein said solid acid catalyst comprises at least one material selected from the group consisting of a zeolite, clay, acid treated metal oxide, acid treated mixed metal oxide, supported heteropoly acid, metal oxide, mixed metal oxide, alumina-silicate, silica, silico-alumino-phosphate, sulphated carbon, proton exchange membrane, acidic ion exchange resin and immobilised Lewis acid catalyst.

7. A process as claimed in claim 1, wherein said hydrocarbon product comprises at least one cyclic aliphatic hydrocarbon.

8. A process according to claim 1 wherein a reaction temperature is in the range from 50-400° C.

9. A process according to claim 1 wherein, in a first step, the oxygenated aromatic feedstock, in the presence of hydrogen, is contacted with the metal hydrogenation catalyst and then, in a second step, the product of said first step is contacted with the solid acid catalyst which is active for the deoxygenation of hydrocarbons.

10. A process according to claim 9, wherein said first step is carried out at a higher temperature than said second step.

11. A process according to claim 9, wherein said second step is carried out at a temperature of 225° C. or less.

12. A process according to claim 9, wherein said second step is carried out in the presence of hydrogen.

13. A process according to claim 12, wherein said second step is carried out in the presence of a metal hydrogenation catalyst.

14. A process according to claim 1, wherein said process is carried out in a single step such that said feedstock is contacted with hydrogen, and a catalyst composition comprising both:
   a) the metal hydrogenation catalyst and
   b) the solid acid catalyst which is active for the deoxygenation of oxygenated hydrocarbons present in the same catalyst bed.

15. A process according to claim 1, wherein a reaction temperature in contact with the solid acid catalyst is not greater than 250° C.

16. The process of claim 1, wherein the metal hydrogenation catalyst and the solid acid catalyst comprise a plurality of formed particles selected from the group consisting of a tablet, an extrudate, and a granule, the formed particles having a minimum dimension of at least 1 mm and a maximum dimension less than 50 mm.

* * * * *